(12) United States Patent
Truckai et al.

(10) Patent No.: US 6,533,784 B2
(45) Date of Patent: Mar. 18, 2003

(54) ELECTROSURGICAL WORKING END FOR TRANSECTING AND SEALING TISSUE

(76) Inventors: Csaba Truckai, 19566 Arden Ct., Saratoga, CA (US) 95070; John H. Shadduck, 1490 Vistazo West, Tiburon, CA (US) 94920

( * ) Notice: Subject to any disclaimer, the term of this patent is extended or adjusted under 35 U.S.C. 154(b) by 0 days.

(21) Appl. No.: 09/792,825

(22) Filed: Feb. 24, 2001

(65) Prior Publication Data

US 2002/0120266 A1 Aug. 29, 2002

(51) Int. Cl.[7] .............................................. A61B 18/18
(52) U.S. Cl. ........................... 606/50; 606/45; 606/48; 606/49
(58) Field of Search ............................. 606/41, 45, 46, 606/47, 48, 49, 50

(56) References Cited

U.S. PATENT DOCUMENTS

| | | | | |
|---|---|---|---|---|
| 5,269,780 A | * | 12/1993 | Roos | 606/42 |
| 5,458,598 A | * | 10/1995 | Feinberg et al. | 606/205 |
| 5,573,535 A | * | 11/1996 | Viklund | 606/37 |
| 5,674,220 A | * | 10/1997 | Fox et al. | 606/205 |
| 5,800,449 A | * | 9/1998 | Wales | 606/170 |
| 6,019,758 A | * | 2/2000 | Slater | 600/566 |
| 6,074,389 A | * | 6/2000 | Levine et al. | 606/45 |
| 6,270,497 B1 | * | 8/2001 | Sekino et al. | 606/42 |
| 6,296,640 B1 | * | 10/2001 | Wampler et al. | 606/48 |

* cited by examiner

*Primary Examiner*—Linda C. M. Dvorak
*Assistant Examiner*—Kenneth Schopfer

(57) ABSTRACT

An electrosurgical working end and method for transecting an anatomic structure along a targeted line and for creating a thermal welds along either of both transected tissue margins, for example for use in a partial lung resection procedure. The working end provides elongate curved or linear guide-track members that can be positioned on opposing sides of the targeted anatomic structure. The working end carries a slidable member with interior channels that receive the guide-track members. The extension member can be moved from a proximal position to an advanced distal position by advancing over the guide-track members. As the extension member advances over the guide-track members (i) the tracks compress the tissue just ahead of the advancing extension member to allow the laterally-outward portion of the extension member to ramp over the tissue, (ii) while contemporaneously a cutting element at the distal end of the extension member transects the tissue. By this means, the transected tissue margins are captured under high compression by working end components on either side of the tissue margin. The working end carries a bi-polar electrode arrangement that engages the just-transected medial tissue layers as well as surface layers to provides Rf current flow for tissue welding purposes that is described as a medial-to-surface bi-polar approach. The system can be used to transect ands seal tissue in a linear or curved line about an anatomic structure such as lung, liver or other bundles of tissue.

21 Claims, 14 Drawing Sheets

ELECTROSURGICAL WORKING END FOR TRANSECTING AND SEALING TISSUE

FIELD OF THE INVENTION

This invention relates to medical devices and techniques and more particularly relates to the working end of an electrosurgical instrument that is adapted for transection and welding of tissue margins in a resection procedure wherein the working end provides highly elongate guide members for guiding a tissue-compressing member over tissue to apply high compressive forces to engaged tissue, and carries elongate Rf electrodes for sealing engaged tissues.

BACKGROUND OF THE INVENTION

In various open and laparoscopic surgeries, it is necessary to seal or weld the margins of transected tissue volumes, for example, in a lung resection. In some procedures, stapling instruments are used to apply a series of mechanically deformable staples to seal the transected edge a tissue volume. Such mechanical devices may create a seal that leaks which can result in later complications.

Various radiofrequency (Rf) surgical instruments have been developed for sealing the edges of transected tissues. For example, FIG. 1A shows a sectional view of paired electrode jaws 2a and 2b of a typical prior art bi-polar Rf grasper grasping two tissue layers. In a typical bi-polar jaw arrangement, each jaw face comprises an electrode and Rf current flows across the tissue between the first and second polarities in the opposing jaws that engage opposing exterior surfaces of the tissue. FIG. 1A shows typical lines of bi-polar current flow between the jaws. Each jaw in FIG. 1A has a central slot adapted to receive a reciprocating blade member as is known in the art for transecting the captured vessel after it is sealed While bi-polar graspers as in FIG. 1A can adequately seal or weld tissue volumes that have a small cross-section, such bi-polar instruments are often ineffective in sealing or welding many types of anatomic structures, e.g., (i) anatomic structures having walls with irregular or thick fibrous content, such as lung tissue; (ii) bundles of disparate anatomic structures, (iii) substantially thick anatomic and structures, and (iv) large diameter blood vessels having walls with thick fascia layers.

As depicted in FIG. 1A, a prior art grasper-type instrument is depicted with jaw-electrodes engaging opposing side of a tissue volume with substantially thick, dense and non-uniform fascia layers underlying its exterior surface, fro example a large diameter blood vessel. As depicted in FIG. 1A, the fascia layers f prevent a uniform flow of current from the first exterior tissue surface s to the second exterior tissue surface s that are in contact with electrodes 2a and 2b. The lack of uniform bi-polar current across the fascia layers f causes non-uniform thermal effects that typically results in localized tissue desiccation and charring indicated at c. Such tissue charring can elevate impedance levels in the captured tissue so that current flow across the tissue is terminated altogether. FIG. 1B depicts an exemplary result of attempting to create a weld across tissue with thick fascia layers f with a prior art bi-polar instrument. FIGS. 1A–1B show localized surface charring c and non-uniform weld regions w in the medial layers m of vessel. Further, FIG. 1B depicts a common undesirable characteristic of prior art welding wherein thermal effects propagate laterally from the targeted tissue causing unwanted collateral (thermal) damage indicated at d.

What is needed is an instrument working end that can utilize Rf energy in new delivery modalities: (i) to weld or seal tissue volumes that are not uniform in hydration, density and collagenous content; (ii) to transect and weld tissue margins contemporaneously in along either linear or curved paths; (iii) to weld a targeted tissue region while substantially preventing collateral thermal damage in regions lateral to the targeted tissue; (iv) to weld a transected margin of a bundle of disparate anatomic structures; and (v) to weld a transected margin of a substantially thick anatomic structure.

SUMMARY OF THE INVENTION

The object of the present invention is to provide an instrument working end capable of transecting and compressing tissue to allow for controlled Rf energy delivery to transected tissue margins that have thick fascia layers or other tissue layers with non-uniform fibrous content. Such tissues are difficult to seal since the fascia layers can prevent uniform current flow and uniform ohmic heating of the tissue.

As background, the biological mechanisms underlying tissue fusion by means of thermal effects are not fully understood. In general, the delivery of Rf energy to a captured tissue volume elevates the tissue temperature and thereby at least partially denatures proteins in the tissue. The objective is to denature such proteins, including collagen, into a proteinaceous amalgam that intermixes and fuses together as the proteins renature. As the treated region heals over time, the so-called weld is reabsorbed by the body's wound healing process.

In order to create an effective weld in a tissue volume dominated by the fascia layers, it has been found that several factors are critical. The objective is to create a substantially even temperature distribution across the targeted tissue volume to thereby create a uniform weld or seal. Fibrous tissue layers (i.e., fascia) conduct Rf current differently than adjacent less-fibrous layers, and it is believed that differences in extracellular fluid contents in such adjacent tissues contribute greatly to the differences in ohmic heating. It has been found that by applying high compressive forces to fascia layers and underlying non-fibrous layers, the extracellular fluids migrate from the site to collateral regions. Thus, the compressive forces can make resistance more uniform regionally within the engaged tissue. Further, it has been found that that one critical factor in creating an effective weld across fibrous (fascia) layers is the delivery of bi-polar Rf energy from electrode surfaces engaging medial layers and surface (fascia) layers. In other words, effective current flow through the fascia layers is best accomplished by engaging electrodes on opposing sides of such fascia layers. Prior art jaw structures that only deliver bi-polar Rf energy from outside the surface or fascial layers cannot cause effective regional heating inward of such fascial layers. For this. reason, the novel technique causes Rf current flow to-and-from exterior the medial (or just-transected) non-fascia layers of tissue at the interior of the structure, rather than to-and-from exterior surfaces only as in the prior art. This method is termed herein a medial-to-surface bi-polar delivery approach or a subfascia-to-fascia bi-polar approach.

Another aspect of the invention provides means for creating high compression forces a very elongate working end that engages the targeted tissue. This is accomplished by providing a slidable extension member that defines channels that engage the entire length elongate guide-track members that guide the extension member over the tissue. The extension member of the invention thus is adapted to provide multiple novel functionality: (i) to contemporaneously transect the tissue and engage the transected tissue margins under high compression within the components of the working end; and (ii) to provide spaced apart longitudinal electrode surfaces for delivery of Rf flow to each transected tissue margin from medial tissue layers to surface layers.

The combination of the extension member in cooperation with the paired flexible guide-track members thus provides an electrode arrangement in engagement with the tissue margins that accomplishes the electrosurgical welding technique of the invention. Certain spaced apart portions of channels in the extension member carry electrode surfaces coupled to an Rf source. Thus, when the extension member is moved to the extended position after transecting the engaged tissue volume, one elongate electrode carried at the center of the extension member engages the medial or interior layers of the transected margin. By this means, bi-polar current flows can be directed from the center portion of the extension member that engages medial or sub-fascial tissue layers to outward portions of the extension member and the guide-tracks that engage opposing surface or fascial tissue layers of the targeted tissue volume. It has been found that by engaging the medial portion of a just-transected structure with a first polarity electrode, and engaging the exterior surfaces of the structure with second polarity electrodes, a substantially uniform current flow through non-uniform fascia layers can be accomplished. This novel medal-to-surface bipolar approach of the invention also reduce or prevent tissue charring, and substantially prevents collateral thermal damage in the tissue by reducing stray Rf current flow through tissue lateral to the engaged tissue.

In another embodiment of the invention, the working end includes components of a sensor system which together with a power controller can control Rf energy delivery during a tissue welding procedure. For example, feedback circuitry for measuring temperatures at one or more temperature sensors in the working end may be provided. Another type of feedback circuitry may be provided for measuring the impedance of tissue engaged between various active electrodes carried by the working end. The power controller may continuously modulate and control Rf delivery in order to achieve (or maintain) a particular parameter such as a particular temperature in tissue, an average of temperatures measured among multiple sensors, a temperature profile (change in energy delivery over time), or a particular impedance level or range.

Additional objects and advantages of the invention will be apparent from the following description, the accompanying drawings and the appended claims.

BRIEF DESCRIPTION OF THE DRAWINGS

FIGS. 4A–4B depicting the positioning of guide members over a targeted transection path in an anatomic structure, and FIG. 4C depicting the advancement of the extension member over the guide tracks.

DETAILED DESCRIPTION OF THE INVENTION

Figure 1A:
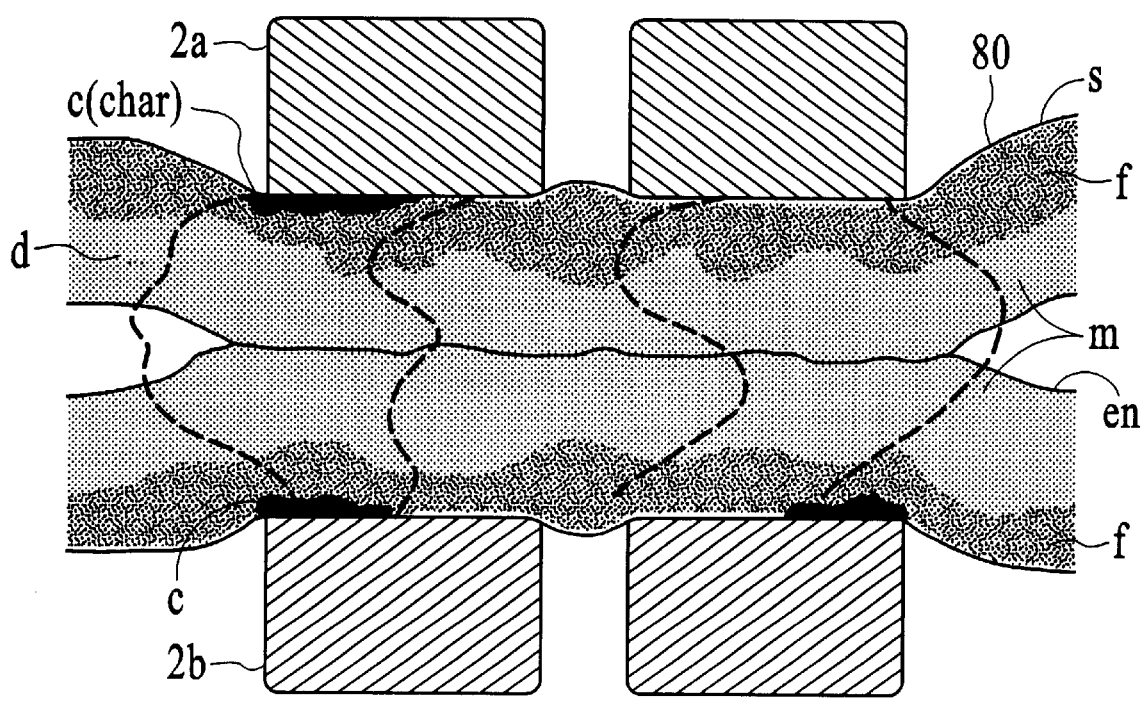
FIG. 1A is an illustration of current flow between the paired jaws of a prior art bi-polar radiofrequency device in a method of sealing a tissue with fascia layers that are resistant to Rf current flow therethrough.
Figure 1B:
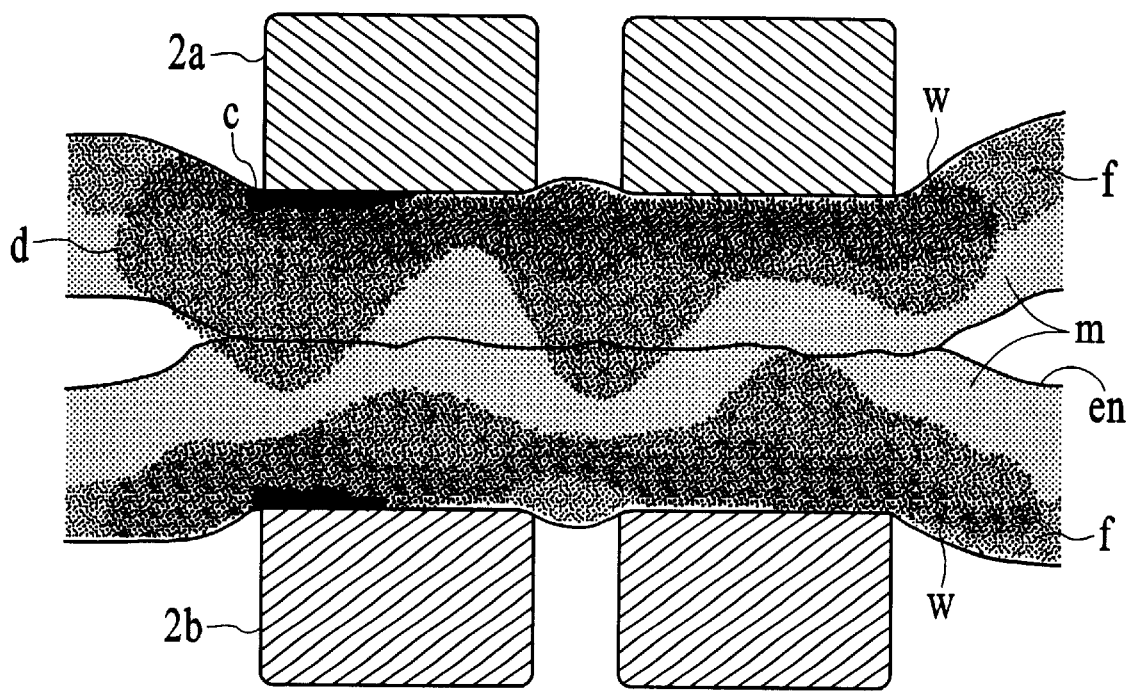
FIG. 1B illustrates representative weld effects of the bi-polar current flow of FIG. 1A.
Figure 2A:
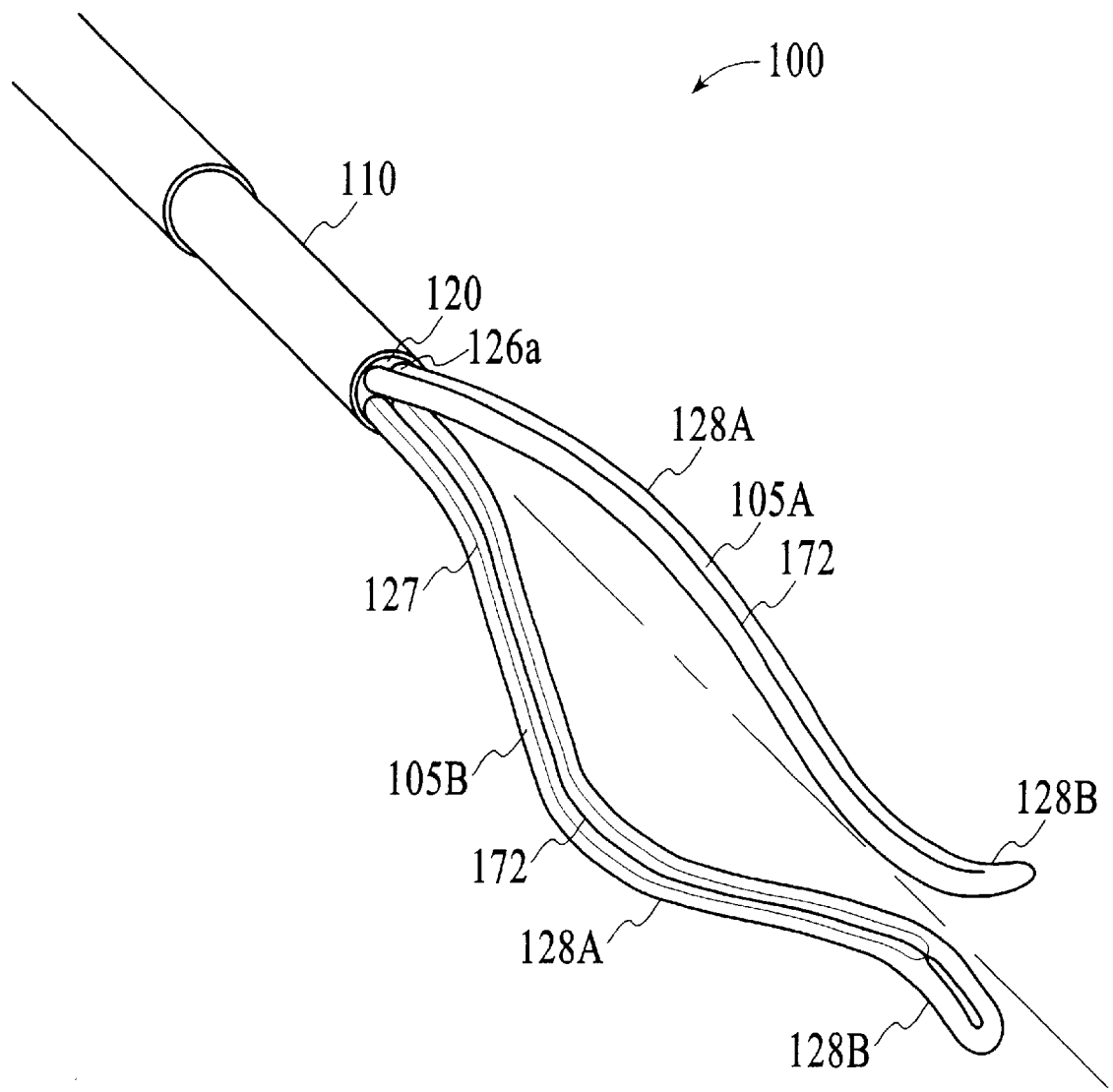
FIG. 2A is a perspective view of a Type "A" working end of the present invention showing first and second guide members extending from the distal end of an introducer, with a cooperating slidable extension member in a retracted position within the introducer.

1. Type "A" Working End for Transecting Tissue and Sealing the Transected Margins. Referring to FIG. 2A, the working end 100 of an exemplary Type "A" embodiment is shown that is adapted for transecting and welding at least one transected tissue margin along a targeted track or path p in tissue, such as lung portion, in an open or endoscopic procedure. The working end 100 has first and second elongate guide members or guide-track members indicated at 105A and 105B that are substantially flexible wire-type elements carried at distal end 108 of an introducer member 110 extending from a proximal handle (not shown). In this Type "A" embodiment, the guide members 105A and 105B extend along a central longitudinal axis 115 and provide multiple functionality: (i) to place over or about a target path p in tissue that is to be transected, (ii) to thereafter guide the terminal portion 118 of an extension member 120 carrying an electrode cutting element 122 along the targeted path p in tissue, and (iii) to provide engagement surfaces 127 for the high-compression engagement of the margins of the transected tissue on both left and right sides of the working end in combination with the extension member 120.

In the exemplary embodiment of FIG. 2A, the structural component of introducer portion 110 has a cylindrical cross-section and comprises a thin-wall tubular sleeve 126 that extends from the proximal handle, although any cross section may be suitable. The diameter of sleeve 126 may range from about 3 mm. to 6 mm., although larger diameter sleeves fall within the scope of the invention. The handle may be any type of pistol-grip or other type of handle known in the art that carries actuator levers or slides to translate the extension member relative to the guide tracks.

Figure 3:
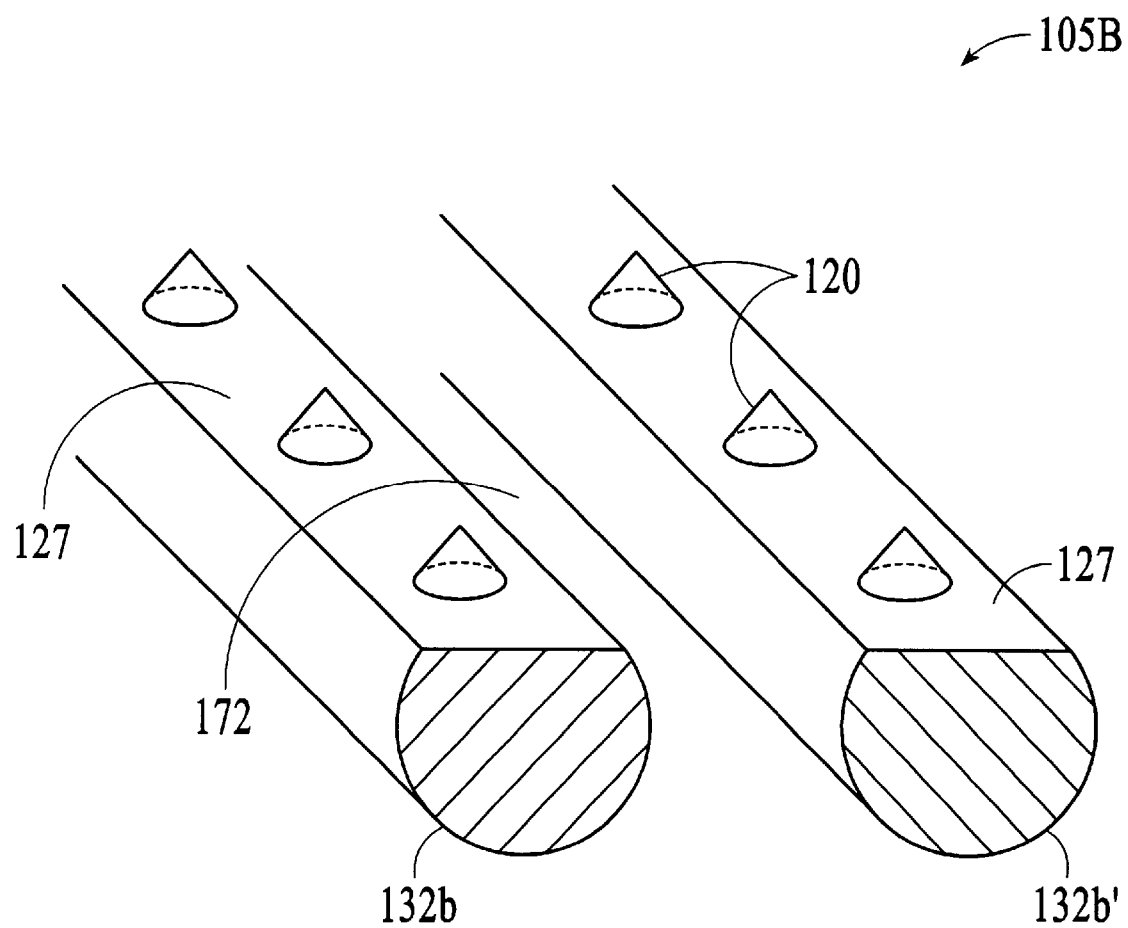
FIG. 3 is sectional view of a guide member of the invention showing tissue-gripping elements.

As can be seen in FIG. 2A, one embodiment of the working end 100 has very elongate guide members 105A and 105B of a flexible round wire or rod element, for example, having a diameter ranging from about 0.03" to 0.10". The cross-section of guide members 105A and 105B can provide engagement surfaces 127 (collectively) that are flat as shown in FIGS. 2A & 3. Serrations, sharp projecting elements or any suitable gripping surface may be impressed on the engagement surfaces 127 to better engage tissue as the extension member is advanced over the guides. FIG. 3 shows exemplary projecting elements 128 (i.e,. spikes) that can be provided in the engagement surfaces 127, which may be particularly useful in the curved guide tracks disclosed in the Type "B" embodiment below.

Figure 4A:
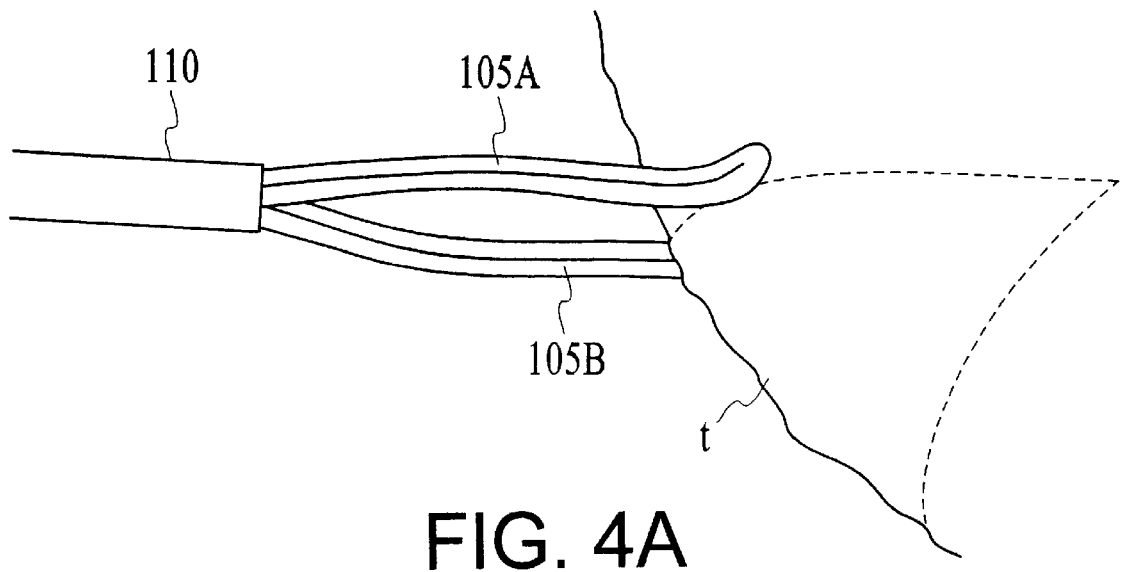
FIGS. 4A–4C are illustrations of initial steps of practicing the method of the invention.
Figure 4B:
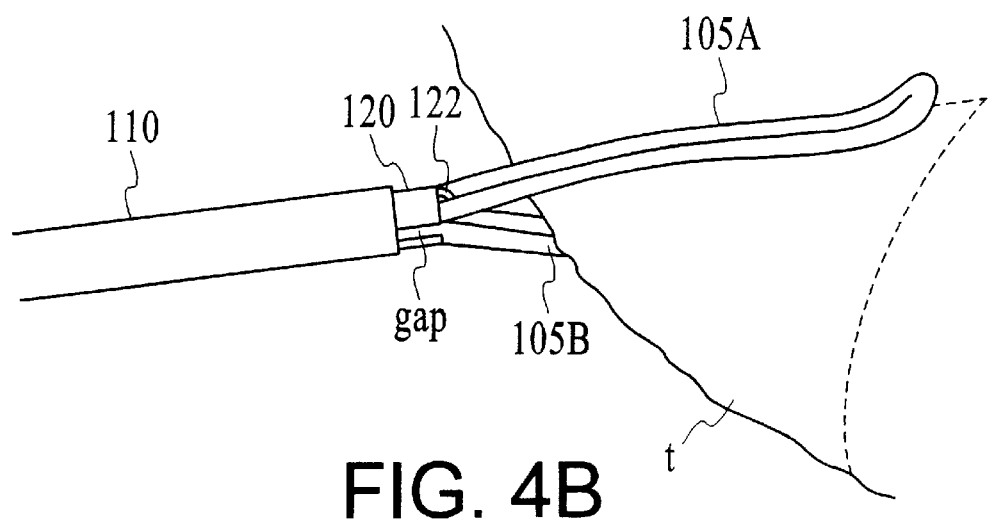
Figure 4C:
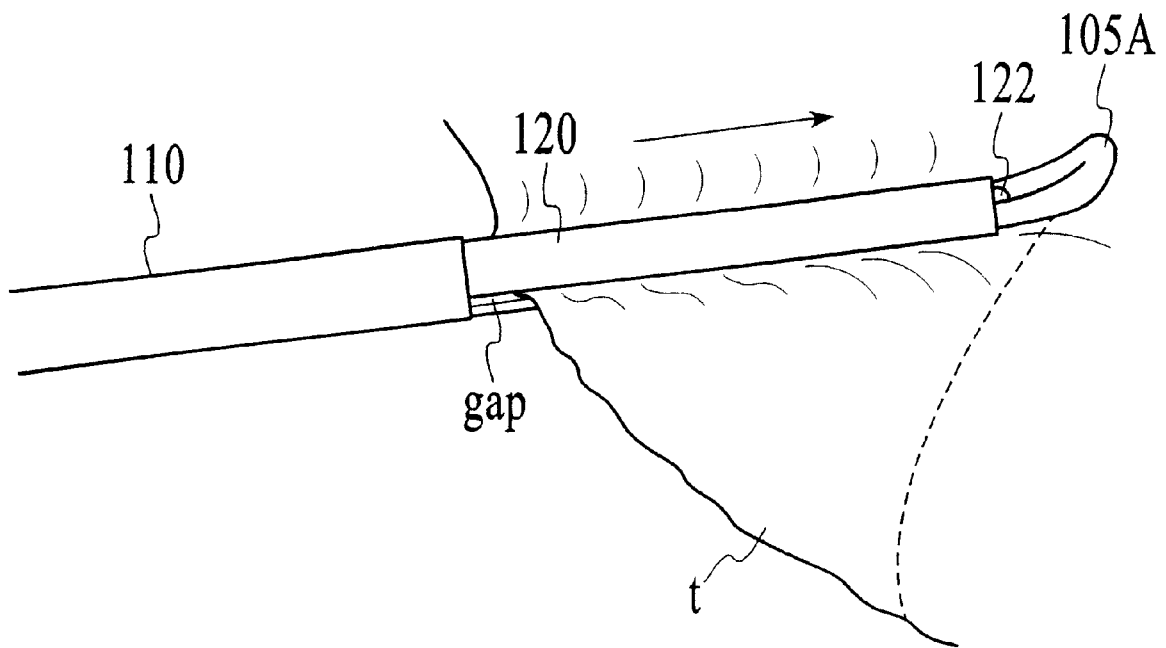

The guide members 105A and 105B in this embodiment define medial outward bowed portions or curve portions indicated at 128A and optional distal angled portions 128B that are adapted to allow guide members 105A and 105B to be pushed over a path p in tissue (see FIG. 4B). It should be appreciated that the shape of the guide members 105A and 105B may be any suitable linear or curved shape to allow ease of placement over a tissue volume targeted for transection. FIGS. 4A–4C illustrate the initial steps of the method of advancing the elongate guide members 105A and 105B over a targeted path in an anatomic structure. FIG. 4A indicates that successive transections along paths $p_1$ and $p_2$ can thus accomplish a wedge resection of a targeted tissue volume while at the same time selectively sealing one or both of the transection margins on either side of each path p.

Figure 2B:
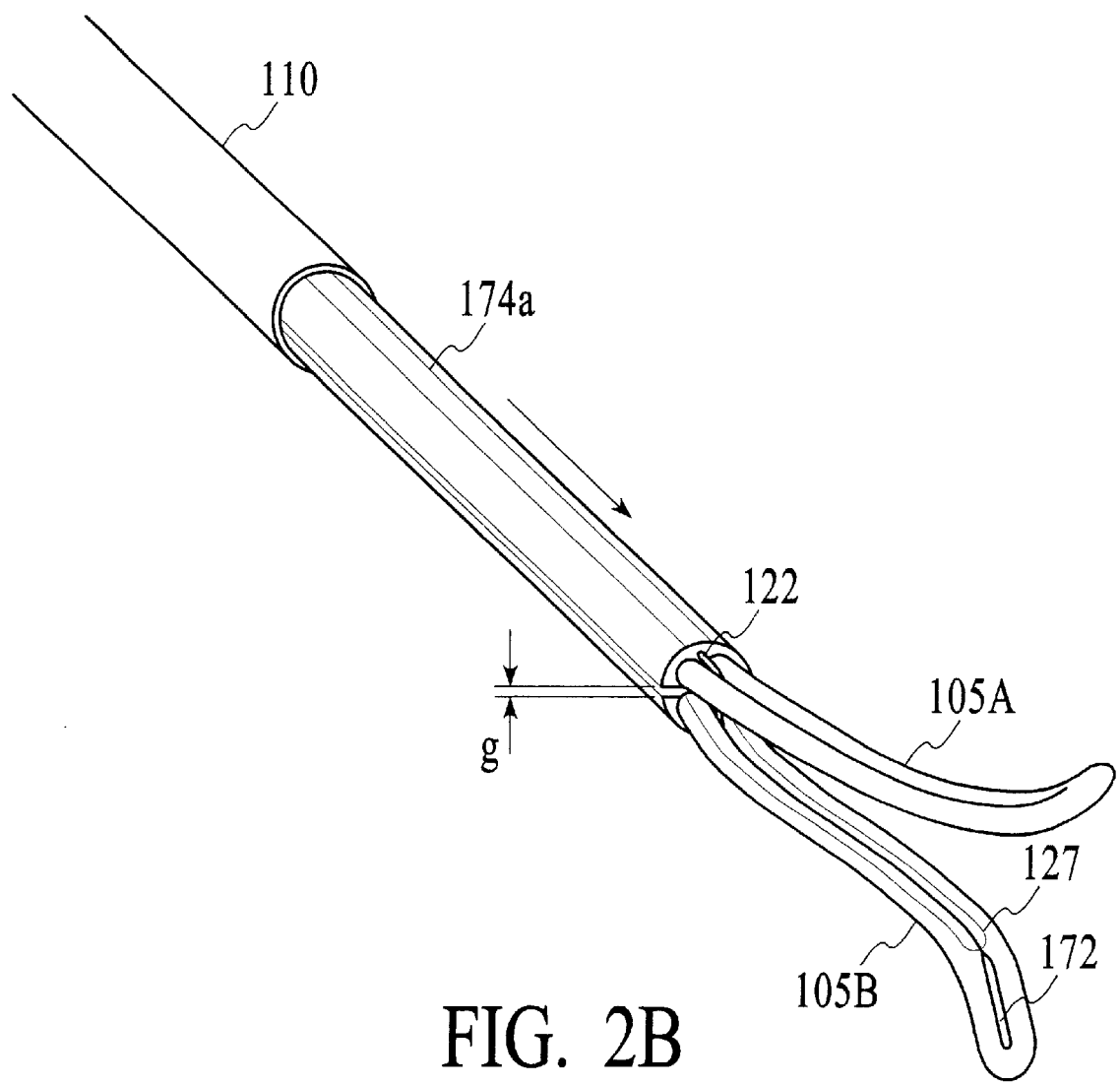
FIG. 2B is another view of the working end of FIG. 2A with the slidable extension member moved toward a extended position over the guide members, the extension member having a distal cutting electrode.

FIGS. 2A & 2B illustrate that guide members 105A and 105B preferably are fabricated of a spring-type metal rod formed with suitable curves 128A and 128B. The guide members 105A and 105B do not comprise jaws in the conventional sense since they are substantially flexible and hence lack jaw-type functionality. That is, the guide members 105A and 105B cannot be moved to a closed position to capture tissue as they provide no inherent strength to be moved between such open and closed positions. Rather, the rod-type elements that make up guide members 105A and 105B are adapted only to guide extension member 120 and to serve as a ramp over the tissue to allow the advancement of extension member 120 over the tissue that otherwise would not be possible. The extension member 120 thus slides over the rod-type guide elements with its terminal cutting element 122 transecting the tissue, in which process the extension member 120 captures the combination of the transected tissue margins and the guide members in a high compression sandwich-like arrangement. It has been found that this means of engaging tissue margins is ideally suited for tissue welding with Rf current. In the exemplary embodiment; the rod-like elements of guide members 105A and 105B comprise paired wire elements, for example, indicated as elements or rods 13 2a and 132a' in guide member 105A and rods 132b and 132b" in guide member 105B (see FIG. 2A). While a metal is a preferred material for guide members 105A and 105B, plastic or composite materials also can be used.

All of the electrosurgical cutting and scaling functionality of the invention is provided in extension member 120 and is described next. As can be seen in FIGS. 2B, 4B–4C & 5, the extension member 120 has a round exterior cross-section and has a first retracted position within the introducer 110 (see FIG. 2A). FIGS. 2B & 4C show views of the extension member 120 being advanced toward a second extended position over the guide members 105A and 105B as its distal cutting element 122 in terminal portion 118 transects the captured tissue t.

Figure 5:
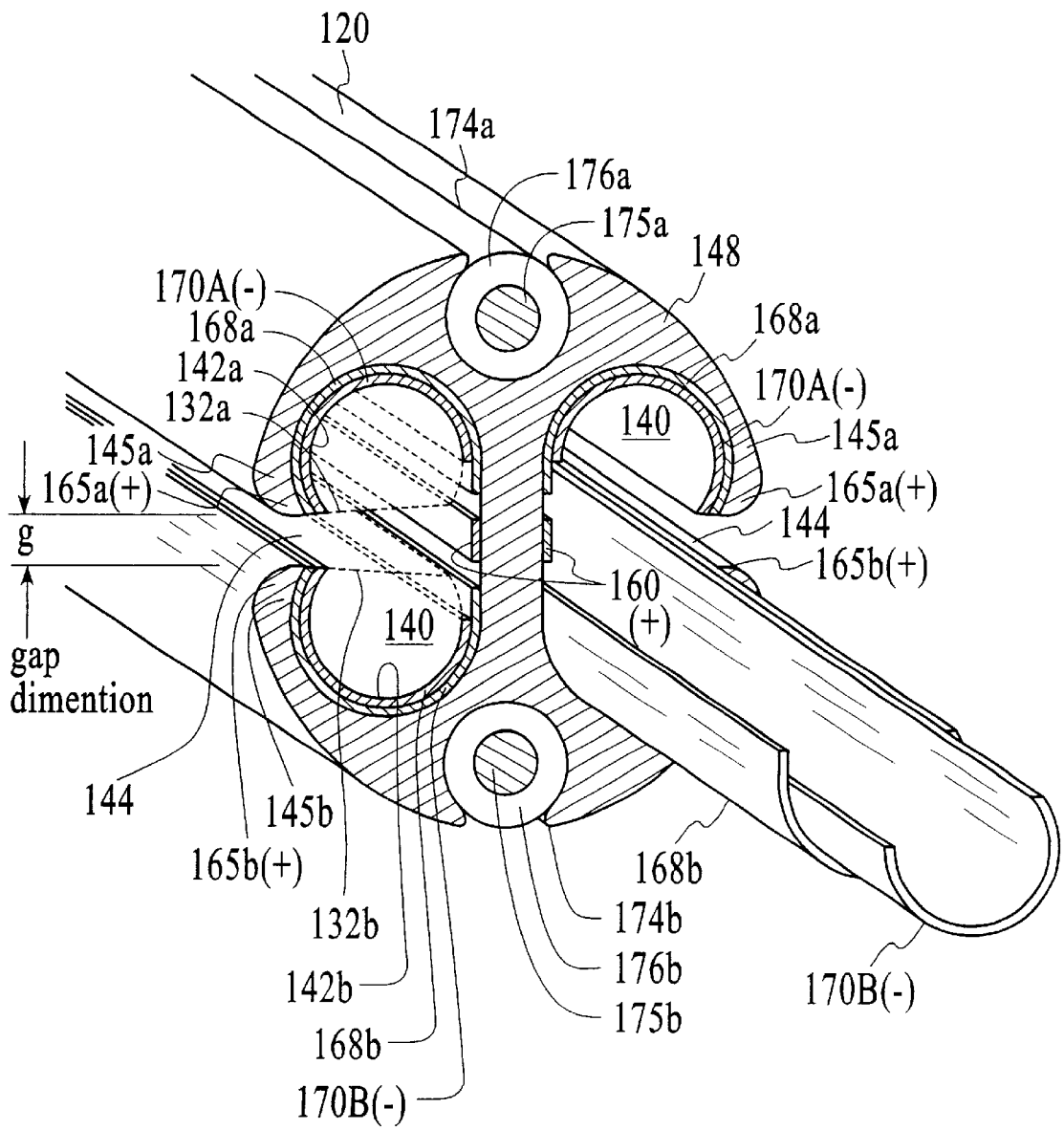
FIG. 5 is an enlarged cross-sectional view of the extension member of FIG. 2B showing the electrode arrangement carried by the extension member.

Now turning to FIG. 5, the sectional view of extension member 120 is shown to explain the various functional components carried therein. In the embodiment depicted in FIG. 5, it can be seen that the extension member 120 has left and right channel portions indicated at 140 (collectively) that are shaped to closely fit around the round rod-type elements of guide members 105A and 105B as the member is slidably moved from its first retracted position toward its second extended position.

For example, FIG. 5 shows a channel 140 at the right side of the instrument (left in view) that has upper surface portions 14 2a about its top and side that slidably engage one element (132a) of guide member 105A about exterior surfaces of that round element. Likewise, FIG. 5 shows a lower part of the channel 140 with surface portions 142b about the bottom and side of another element (132b) of the lower guide member 105B that slidably engages an exterior of that element. It thus can be seen how the extension member slides over guide members 105A and 105B and flexes the guide members toward one another to allow the entire assembly to compress very tightly about the opposing surfaces of the captured tissue t as the leading edge electrode 122 transects the tissue. The extension member 120 defines a longitudinal slot 144 that extends from each channel 140 to an exterior of the extension member that receives the tissue margin. The slot 144 of extension member 120 thus defines a predetermined gap dimension indicated at g that comprises a selected dimension to which the captured tissue will be compressed (see FIGS. 3C & 5). The distal end of the gap g (not shown) preferably tapers from a more open dimension to a tighter dimension to initially allow the extension member to slide over engaged tissue. The extension member 120 further defines laterally outward portions 145a and 145b above and below slot 144 that engage the tissue margin. It has been found that tissue should be compressed under high forces for effective Rf welding and the gap g can be substantially small for many tissues. It can be appreciated that the extension member in combination with guide members 105A and 105B can apply very high compressive forces over a long path in tissue for purposes of transection that would not possible with a conventional jaw-type instrument.

The extension member 120 depicted in FIG. 5 can be fabricated by in alternative materials (either plastic or metal) by extrusion processes known in the art, or it can be made by various casting methods if made in a conductive metal. One preferred embodiment as depicted in FIG. 5 provides a body 148 of the extension member that is fabricated of any suitable conductive material such as a metal. The proximal end of the extension member 120 is coupled by an electrical lead (not shown) to an electrical source 150 and controller 155. Thus, the extension member 120 carries electrical potential to serve as an electrode body. The body 148 of the extension member has cooperating electrode surface portions 160 and 165a–165b that are exposed to contact the captured tissue: (i) at the transected medial tissue that interfaces the exposed electrode surface indicated at 160, and (ii) at opposed exterior surfaces of the captured tissue that interface the exposed electrode surfaces 165a and 165b at upper and lower portions (145a and 145b) of extension member 120 outboard (laterally outward) of channel 140. For purposes of illustration, these exposed electrode surface portions 160 and 165a–165b are indicated in FIG. 5 to have a positive polarity (+) to cooperate with negative polarity (−) electrodes described next. These opposing polarity electrodes are, of course, spaced apart from one another and coupled to the electrical source 150 that defines the positive and negative polarities during operation of the instrument. In FIG. 5, it should be appreciated that the left and right sides of the extension member are mirror images of one another with reference to their electrode arrangements. Thus, sealing a tissue margin on either side of the extension member is independent of the other-after the targeted tissue is transected and captured for such Rf welding or sealing as in FIG. 4C. For simplicity, this disclosure describes in detail the electrosurgical methods of sealing a transected tissue margin on one side of the extension member, with the understanding that mirror image events also (optionally) occur on the other side of the assembly.

Still referring to FIG. 5, thin insulator layers 168a and 168b of any suitable plastic or ceramic extend in a partial radius around upper and lower portions of channel 140. Inward of the thin insulator layers 168 are opposing (−) polarity electrodes 170A and 170B that constitute radial sections of elongate hypotubes fitted in the channel and therefore comprise inner surface portions of the channel 140. These longitudinal negative (−) polarity electrodes 170A and 170B, for example of stainless steel, provide the additional advantage of being durable for sliding over the rod elements 132a and 132b that make up portions of guides 105A and 105B. It can be seen that all electrical connections are made to extension member 120 which carries the actual opposing polarity electrodes, thus simplifying fabrication and assembly of the component parts of the working end.

As described above, the distal terminal portion 118 of extension member 120 carries an electrode cutting element indicated at 122 in FIGS. 2B, 4B & 4C. In FIG. 2B, it can be seen that electrode cutting element 122 moves with the gap 172 between the paired rod-type elements that comprise each guide member 105A and 105B. FIG. 5 shows that grooves 174a and 174b are provided in the extension member 120 to carry electrical leads 175a and 175b to the cutting electrode 122. These electrical leads 175a and 175b are insulated from the body 148 of extension member 120 by insulative coatings indicated at 176a and 176b.

Now turning to FIGS. 4C & 6, the operation and use of the working end 100 of FIG. 2A in performing a method of the invention can be briefly described as follows. FIG. 4C depicts the extension 120 being advanced from a proximal position toward an extended distal position as it ramps over the tissue by advancing over the guide-track members that compress the tissue just ahead of the advancing extension member. The laterally-outward portions 145a and 145b of the extension member thereby slide over and engage the just-transected tissue margins contemporaneous with the cutting element 122 transecting the tissue. By this means, the transected tissue margins are captured under high compression by working end components on either side of the margins. FIG. 5 thus depicts the targeted tissue margins t captured between upper and lower portions of the extension member outward of channels 140. The targeted tissue t may be any soft tissue or anatomic structure of a patient's body. The targeted tissue is shown with a surface or fascia layer indicated at f and medial tissue layers m. While FIGS. 4B–4C depict the tissue being transected by a high voltage Rf cutting element 122, it should be appreciated that the cutting element also can be a blade member.

Figure 6:
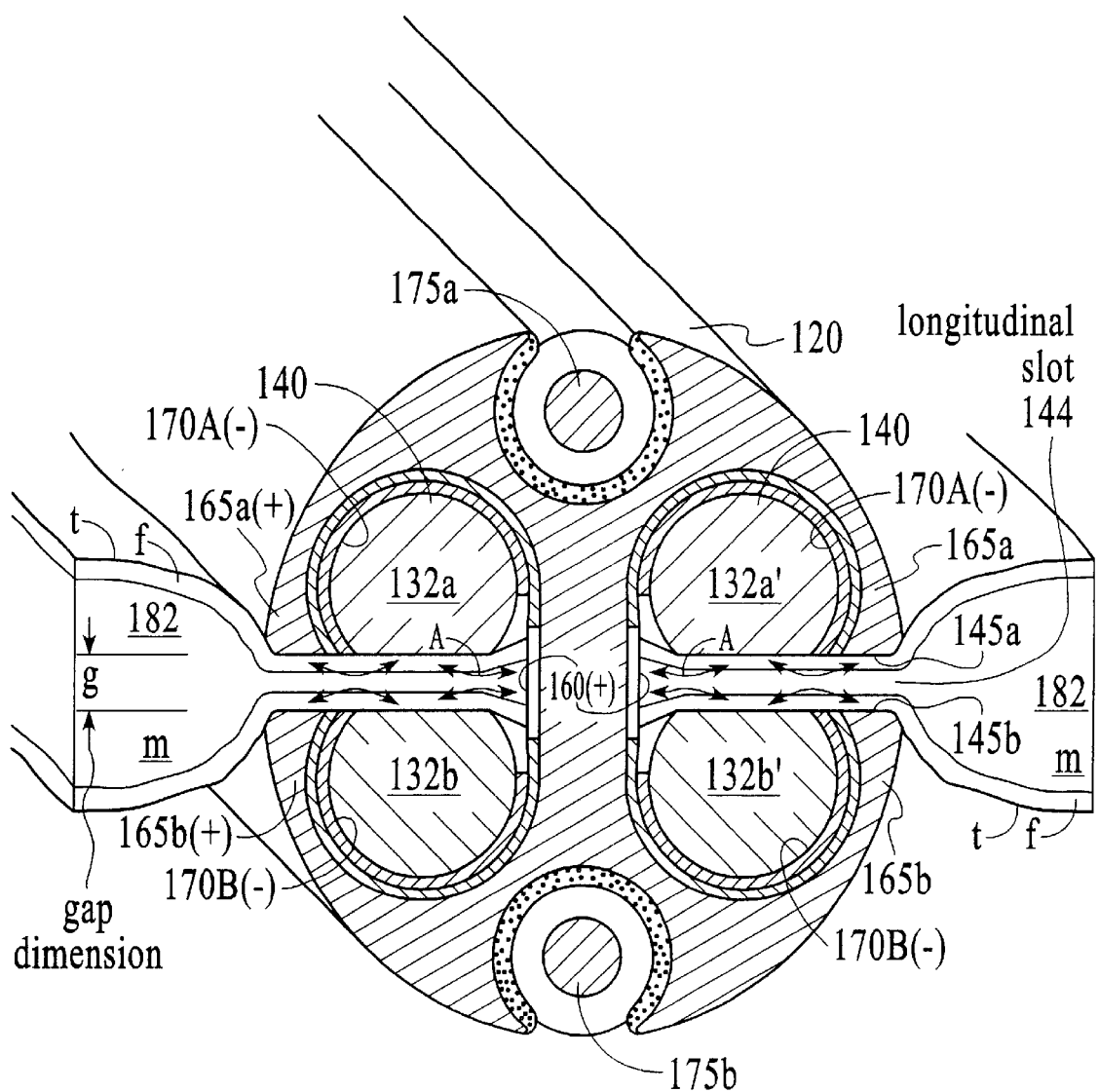
FIG. 6 is a sectional illustration of the extension member of FIG. 5 illustrating the manner of delivering bi-polar Rf current flow to seal or weld a transected tissue margin under high compression.

FIG. 6 provides an illustration of one preferred manner of Rf current flow that causes a sealing or welding effect by the medial-to-surface bi-polar current flow (or vice versa) indicated by arrows A. It has been found that a substantially uniform weld can be created across the captured tissue margin by causing current flow from exposed electrode surfaces 165A and 165B to the electrodes 170A and 170B that further conducts current flow through conductive guide rod elements 132a and 132b. In other words, the sectional illustration of FIG. 6 shows that a weld can be created in the captured tissue margin where proteins (including collagen) are denatured, intermixed under high compressive forces, and fused upon cooling to seal or weld the transected tissue margin. Further, it is believed that the desired weld effects can be accomplished substantially without collateral thermal damage to adjacent tissues indicated at 182 in FIG. 6.

Another embodiment of the invention (not shown) includes a sensor array of individual sensors (or a single sensor) carried in any part of the extension member 120 or guide member 105A–105B that contacts engaged tissue. Such sensors preferably are located either under an electrode 170A–170B or adjacent to an electrode for the purpose of measuring temperatures of the electrode or tissue adjacent to an electrode during a welding procedure. The sensor array typically will consist of thermocouples or thermistors (temperature sensors that have resistances that vary with the temperature level). Thermocouples typically consist of paired dissimilar metals such as copper and constantan which form a T-type thermocouple as is known in the art. Such a sensor system can be linked to feedback circuitry that together with a power controller can control Rf energy delivery during a tissue welding procedure. The feedback circuitry can measure temperatures at one or more sensor locations, or sensors can measure the impedance of tissue, or voltage across the tissue, that is engaged between the electrodes carried by the working end. The power controller then can modulate Rf delivery in order to achieve (or maintain) a particular parameter such as a particular temperature in tissue, an average of temperatures measured among multiple sensors, a temperature profile (change in energy delivery over time), a particular impedance level or range, or a voltage level as is known in the art.

Figure 7:
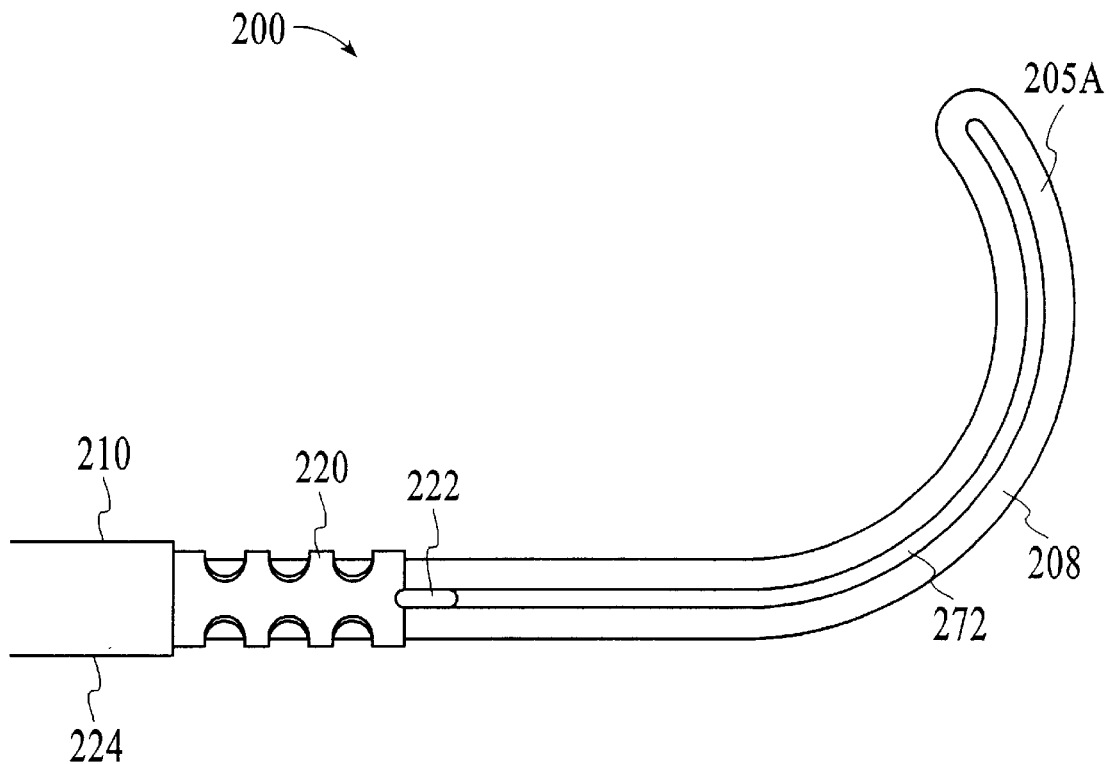
FIG. 7 is a plan view from above a Type "B" working end showing guide members of a shape memory material in an arcuate shape for resecting an arc-like tissue margin.

2. Type "B" Working End for Transecting Tissue and Sealing Tissue Margins. Referring to FIG. 7, the working end 200 of an exemplary Type "B" embodiment is shown that again is adapted for transecting and welding at least one transected tissue margin—this time along an arc-like path p in tissue. FIG. 7 is a plan view from above the working end 200 illustrating elongate guide members 205A and 205B of a substantially flexible wire-type elements that are curved an a selected arc indicated at 208. The upper and lower guide members 205A and 205B are coupled to the distal end of an introducer 210 as described previously. An extension member 220 operates as described previously to slide over the guide members 205A and 205B and carries a distal cutting electrode 222, except in this embodiment the extension member 220 is made of a material of composition of materials that allow it to be guided in the arc defined by the guide members 205A and 205B.

In one embodiment, for example for use in an open surgical procedure, the guide members 205A and 205B are of a somewhat rigid or stiff material that defines the selected arc 208. More preferably, for example for endoscopic procedures, the guide members 205A and 205B are of a shape memory material such a Nitinol that allows the assembly of the extension member 220 and the guide members 205A and 205B to assume a linear configuration and be retracted into sleeve 224 of the introducer (see FIG. 7).

Figure 8:
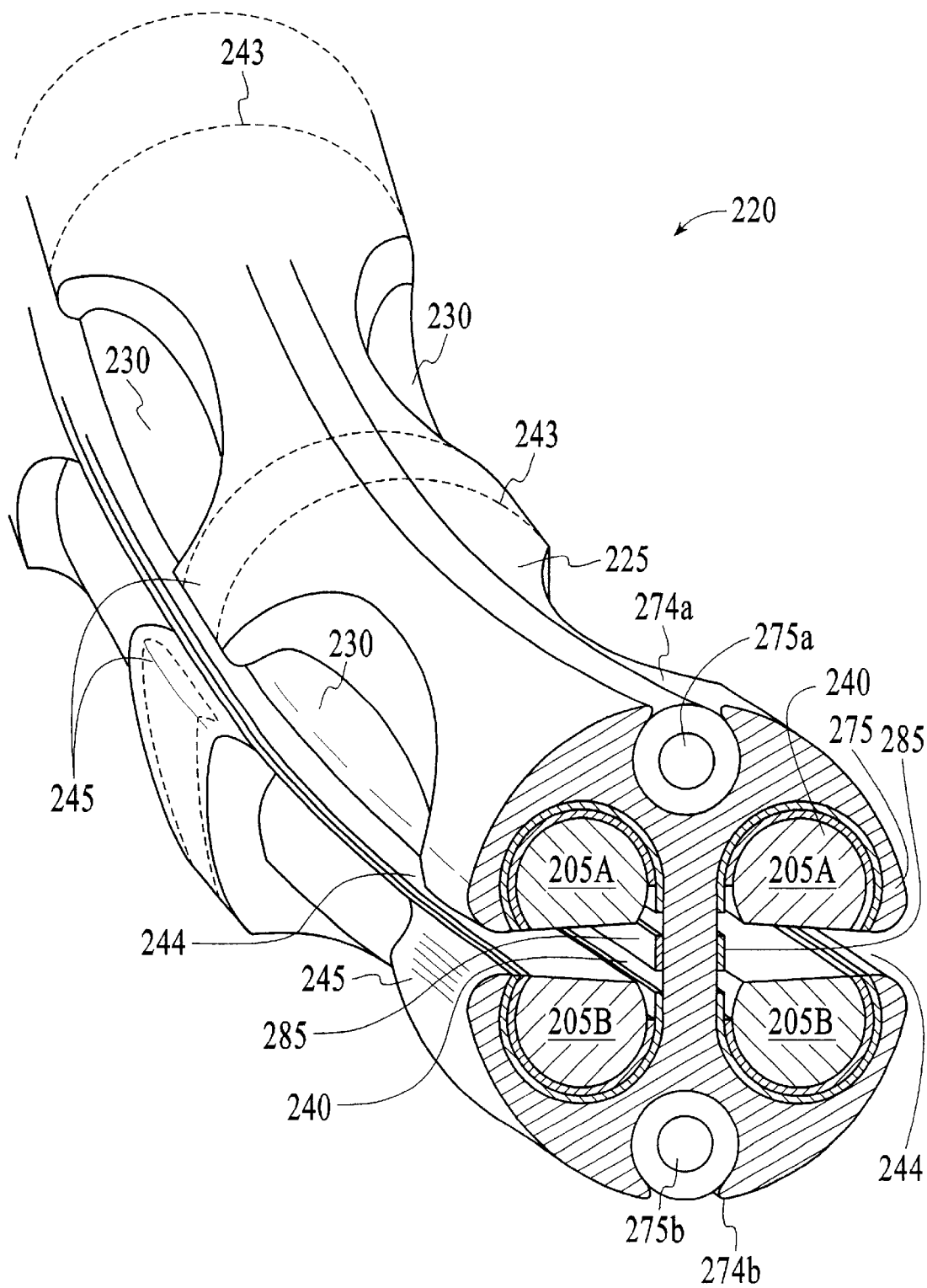
FIG. 8 is a perspective view of a portion of a flexible extension member that cooperates with the arcuate guide members of the Type "B" working end of FIG. 7.

FIG. 8 shows a sectional view of the extension member 220 and illustrates a manner of fabricating the member to be substantially flexible to bend laterally to slide over arcuate guide members 205A and 205B. In this exemplary embodiment, the extension member 220 is unitarily molded of any suitable plastic with a backbone portion indicated at 225 that is defined by a plurality of scallops or cuts 230 (collectively) that are provided laterally to the backbone in left and right sides of the extension member. It can easily be seen how extension member 220 thus can bend laterally as depicted by the arrows in FIG. 8 to follow the curve of the guide members. In this embodiment, the guide members preferably have gripping elements in their tissue engaging surfaces 232 (not shown) insure that the guide members do not slip from the targeted tissue engagement path as the extension member is advanced over tissue. Further, this embodiment shows canted opposing engagement surfaces of the guide members 205A and 205B into pinch the outer portions of the compressed tissue to prevent Rf flow and collateral thermal damage outward of the extension member. As can be seen in FIG. 7, the extension member 220 has channels 240 that slidably cooperate with guide members 205A and 205B in the same manner as the Type "A" embodiment described above. The longitudinal slots 244 define gap dimension g in both sides of extension member 220 that defines the compressed dimension of the engaged tissue margin—again similar to the Type "A" embodiment. In order to insure that the flexible material of the extension member 220 has sufficient strength to maintain the shape of channels 240 as the extension member is advanced over tissue, a series of strong metal shape-maintaining clips 243 (phantom view) can be fitted over backbone 225 of the extension member and over the outboard portions 245 of the extension member that carry the channel portions that slide over guide members 205A and 205B. As can be seen in FIG. 7, the distal termination of extension member 220 carries an electrode cutting element indicated at 222. The electrode cutting element 222 moves within the slot 272 between the paired elements that comprise each guide member 105A and 105B. FIG. 8 also shows that grooves 274a and 274b are provided in the extension member 220 to carry electrical leads 275a and 275b to the distal electrode cutting element, as in the Type "A" embodiment.

The extension member 220 depicted in FIG. 8 can be constructed to carry an electrode arrangement as described in the Type "A" embodiment. However, one preferred embodiment as depicted in FIG. 8 provides the body portion 278 of extension member of a non-conductive plastic. In this exemplary embodiment, the extension member 220 does not carry electrical potential to serve as an electrode body. The extension member 220 carries a central electrode 285 with exposed surfaces in each channel 240 that are exposed to contact the transected medial tissue that interfaces these electrode surfaces. The guide members 205A and 205B themselves comprise the opposing polarity electrodes as indicated by the positive (+) and negative (−) polarity indications in FIG. 8.

Figure 9:
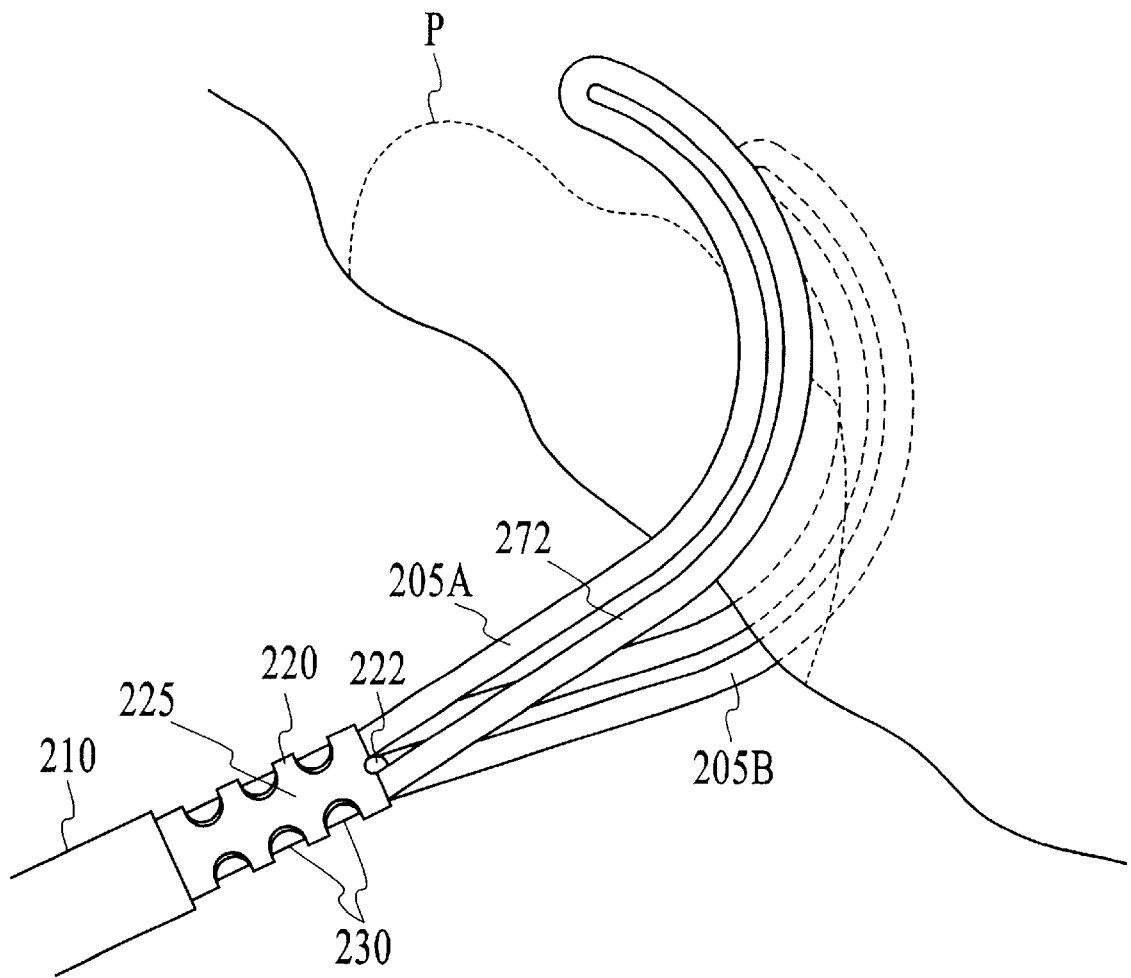
FIG. 9 is a view of the arcuate guide members of the Type "B" working end of FIG. 7 preparing to engage tissue to thereafter accomplishing an arc-like resection.
Figure 10:
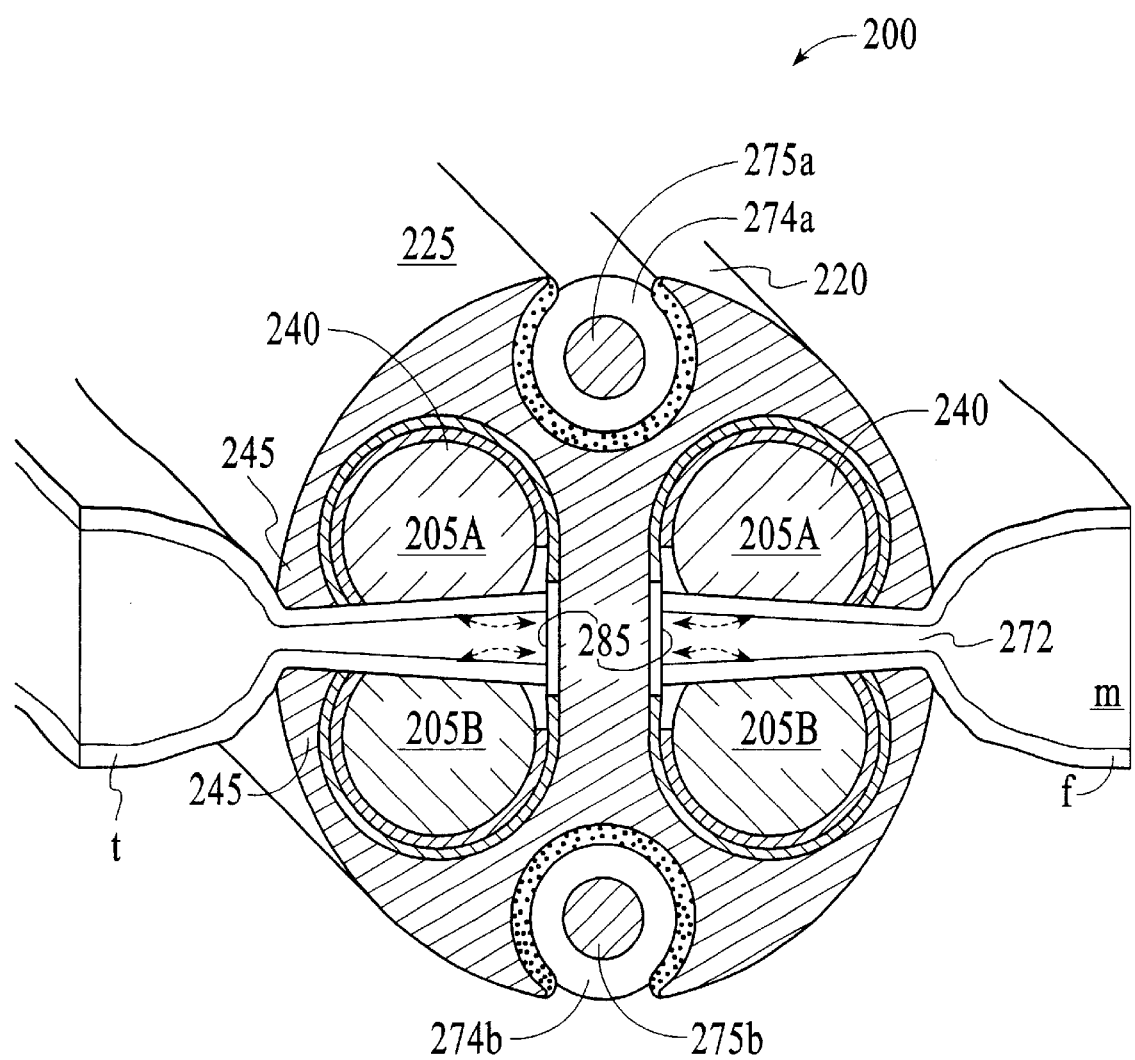
FIG. 10 is a sectional view of the Type "B" working end of FIG. 7 engaging tissue and further depicting Rf current flow.

FIG. 9 shows the working end being prepared to engage tissue along path p to accomplish a tissue resection with sealing of the transected margins. FIG. 10 illustrates a manner of delivering Rf current flow from the central electrode 285 to the opposing polarity guide members 205A and 205B to weld the tissue margins. The Rf current paths again are from a medial tissue to the surfaces of the captured tissue.

Figure 11:
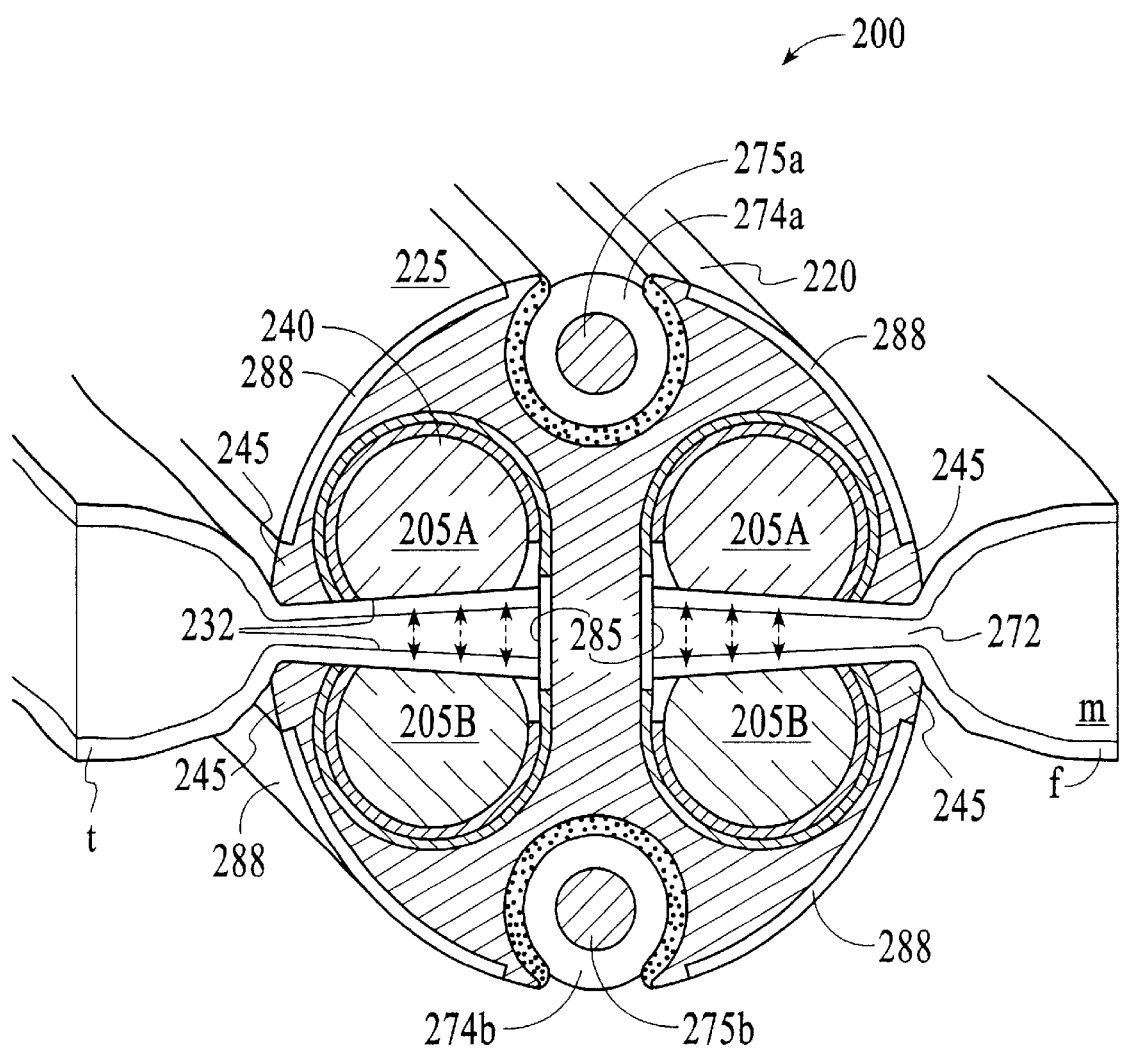
FIG. 11 is a sectional view of an alternative Type "B" working end engaging tissue and depicting another manner of delivering Rf current flow with a multiplexer.

FIG. 11 shows that the same working end 200 of FIGS. 7–10 can be used with an electrical source 150 and controller 155 provided with a multiplexer to deliver Rf current to various paired electrodes. In such an embodiment, each of the upper and lower guide members 205A and 205B and central electrode 285 are coupled by separate leads to the multiplexer and source 150 to allow the guide members 205A and 205B to be multiplexed or switched between common and opposing polarities. FIG. 11 depicts an optional manner of delivering Rf current flow across the engaged tissue margin, for example from the positive (+) polarity upper guide member 205A to a negative (−) polarity lower guide member 205B while the central electrode is without electrical potential.

FIG. 11 also shows other surface electrode surfaces indicated at 288 that are carried within the non-conductive extension member 220 that can be used for surface coagulation of tissue. It has been found that such surface Rf delivery capabilities are useful in an endoscopic intervention in preparation for an actual transection procedure.

The preferred Type "B" embodiment has upper and lower guide members 205A and 205B that are of shape memory material to allow a first linear shape and a second curved shape. However, it should be appreciated that other means known in the art may be used to provide the guide members 205A and 205B in a first linear shape and a second curved shape. For example, for open surgeries, the guide members may be malleable or deformable metal elements that can be manually manipulatable to a desired curved shape. For endoscopic surgeries, the guide members may be deflectable and comprise tubular members fabricated in the manner of microcatheters known in the art that carry pull wires in the walls thereof to deflect the distal portions of the members.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and arc intended to fall within the scope of the appended claims.

What is claimed is:

1. A working end of an electrosurgical transecting-sealing instrument, comprising:
    paired elongate guide members extending along an axis, the guide members coupled to the distal end of an introducer,
    a slidable extension member moveable from a first retracted position to a second extended position relative to the paired guide members, the extension member defining at least one longitudinal channel that engages outer surface portions of said guide members;
    a cutting element carried at the distal termination of the extension member; and
    an elongate electrode surface carried in said at least one channel of the extension member.

2. The working end of claim 1 wherein the extension member carries a longitudinal opening extending from each said channel to the exterior of the extension member for slidable deployment over a transected tissue margin.

3. The working end of claim 1, comprising first and second opposing polarity electrode surfaces carried in each said channel.

4. The working end of claim 1, comprising a plurality of elongate first polarity electrodes surfaces and at least one elongate second polarity electrode surfaces carried in a spaced apart arrangement in each said channel.

5. The working end of claim 1 wherein an electrode surface comprises a channel portion that slidably contacts a guide member.

6. The working end of claim 1 wherein an electrode surface comprises a channel portion that does not contact a guide member.

7. The working end of claim 1 wherein each guide member comprises two substantially parallel elongate elements defining a gap therebetween.

8. The working end of claim 1 wherein the cutting element is selected from the class consisting of cutting electrodes and cutting blades.

9. The working end of claim 7 wherein the cutting element is moveable from a first retracted position to a second extended position within the gap between the two substantially parallel elongate elements that comprise the guide members.

10. A method of using an electrosurgical working end to transect and seal tissue, comprising:

(a) positioning first and second elongate guide members on opposing sides of tissue along a transaction line, the guide members coupled to the distal end of an introducer;

(b) sliding an elongate member from a first proximal position to a second extended position over the first and second elongate guide members, wherein longitudinal channels in said elongate member engage outer surface portions of the guide members;

(c) wherein a cutting element carried about the distal end of the elongate member transects the tissue along the transection line and contemporaneously compresses a transected tissue margin between portions of the working end disposed on opposing sides of the tissue; and (d) delivering Rf current to the tissue margin compressed within the working end from at least one electrode surface carried by the elongate member thereby sealing the tissue margin.

11. The method of claim 10, wherein step (d) delivers Rf current between a first polarity electrode engaging medial layers of the transected tissue margin and a second polarity electrode engaging surface layers of the engaged tissue margin.

12. The method of claim 10, wherein step (d) delivers Rf current between first and second polarity electrodes engaging opposing surface layers of the transected tissue margin.

13. The method of claim 10, wherein step (d) delivers Rf current in a multiplexed manner between first and second polarity electrodes engaging medial and surface layers, respectively, and between first and second polarity electrodes engaging opposing surface layers of the transected tissue margin.

14. The method of claim 10, wherein step (c) utilizes a cutting electrode to transect tissue.

15. The method of claim 10, wherein step (c) utilizes a cutting blade to transect tissue.

16. A working end of an electrosurgical instrument for transecting and sealing tissue, comprising:

first and second moveable guide members coupled to a distal end of an introducer portion;

an extension member defining first and second longitudinal interior channels that slidably engage outer surface portions of each guide member, and further defining a longitudinal slot extending between each channel and an exterior of the extension member;

a cutting element carried about the distal terminus of the extension member, and an electrode surface extending substantially along the working length of each said channel of the extension member.

17. The working end of claim 16 wherein each said interior channel defines a laterally outward surface portion and a laterally inward surface portion, with each laterally inward and outward surface carrying an elongate electrode.

18. The working end of claim 16 wherein each guide member is of a shape memory material.

19. The working end of claim 18 wherein each guide member has a first repose shape that extends in a substantial curve and is capable of deformation to a second linear shape.

20. The working end of claim 16 wherein the extension member is of a flexible material to allow lateral bending thereof.

21. The working end of claim 16 wherein the guide members arc of an electrically conductive material.

* * * * *